United States Patent

Verreet et al.

[11] Patent Number: 5,156,597
[45] Date of Patent: Oct. 20, 1992

[54] TRANSCUTANEOUS IMPLANTATION CATHETER

[75] Inventors: Patrick Verreet, Meerbusch; Claus Haacke, Melsungen, both of Fed. Rep. of Germany

[73] Assignee: B. Braun Melsungen AG, Melsungen, Fed. Rep. of Germany

[21] Appl. No.: 630,265

[22] Filed: Dec. 19, 1990

[30] Foreign Application Priority Data

Dec. 30, 1989 [DE] Fed. Rep. of Germany ....... 3943412

[51] Int. Cl.⁵ ............................................. A61M 5/32
[52] U.S. Cl. .................................. 604/175; 604/280
[58] Field of Search ................. 604/29, 174, 175, 264, 604/280; 623/11

[56] References Cited

U.S. PATENT DOCUMENTS

| | | | |
|---|---|---|---|
| 4,184,497 | 1/1980 | Kolff et al. | 604/29 X |
| 4,266,999 | 5/1981 | Baier | 604/175 X |
| 4,392,855 | 7/1983 | Oreopoulus et al. | 604/175 |
| 4,588,461 | 5/1986 | Braun . | |
| 4,634,422 | 1/1987 | Kantrowitz et al. | 604/49 |
| 4,946,444 | 8/1990 | Heimke et al. | 604/175 |
| 4,950,259 | 8/1990 | Geary et al. | 604/282 |
| 5,057,075 | 10/1991 | Moncrief et al. | 604/49 |
| 5,085,632 | 2/1992 | Ikada et al. | 604/29 |

FOREIGN PATENT DOCUMENTS 0164896 12/1985 European Pat. Off. .
2806030 8/1979 Fed. Rep. of Germany .

OTHER PUBLICATIONS

German periodical "Der Chirurg" (1983), pp. 609-612.

Primary Examiner—John D. Yasko
Assistant Examiner—Adam J. Cermak
Attorney, Agent, or Firm—Spensley Horn Jubas & Lubitz

[57] ABSTRACT

Intermediate an intracorporal first section and an extracorporal third section, a transcutaneous implantation catheter has a second section entirely consisting of an open-pore fiber fabric having a porous outer surface. It is particularly advantageous for a fast growing-in process that is not inflammatory and for a good transition from the subcutaneous connective tissue to the area of the skin epithelium, if the porosity (the spaces between the fabric fibrils) increases from the inside to the outside of the catheter. This allows the tissue to grow into the second section of the catheter. The implantation tunnel closes completely so that no liquid collections are allowed to be formed between the catheter and the tissue. The risk of infections is reduced. The first section is of the same material as the second section, but has a smooth surface and a wall of solid material.

14 Claims, 3 Drawing Sheets

TRANSCUTANEOUS IMPLANTATION CATHETER

BACKGROUND OF THE INVENTION

1. Field of the Invention

The invention relates to a transcutaneous implantation catheter. Besides providing access to blood vessels and other cavities in the human body, the present invention is also applicable in the field of peritoneal dialysis.

2. Description of Related Art

A continuous ambulant peritoneal dialysis (CAPD) requires peritoneal catheters that lead through the abdominal wall of a patient and are enclosed therein by tissue. A peritoneal catheter is known from German periodical "Der Chirurg" (1983), pages 609–612, which consists of a continuous hose comprising three sections. Between a intraperitoneal first section and a second section intended to be encapsulated by tissue in the abdominal wall, there are retaining elements in the form of a sleeve for delimiting the abdominal wall section of the hose, a Dacron disc and a silastic ball for fixing the catheter to the lamina posterior of the rectus sheath. Between the second section and the extracorporal third section, there is a Dacron sleeve for anchoring in the subcutis. This known peritoneal catheter generally consists of a silicone hose. The second section, destined to be set into the tissue of the muscle or the skin, causes the growing of a smooth enclosing tissue sheathing in the implantation tunnel in the tissue between the points of concretion formed by the sleeve and the disc, the tissue sheathing not adhering to the catheter. Liquid gathers in the gap between the catheter and the enclosing sheathing, which can easily be infected. Moreover, it has been found out that this area is continuously subjected to a strong reaction between fibroblasts, macrophages and skin cells due to the use of Dacron sleeves in the area of the skin, where the tissue grows around the catheter. This reaction often leads to inflammations.

Further, percutaneous means of access are known that grow together with the body tissue and form a location of access for a catheter to be inserted. Such a means of access is described in European Patent Application 0 164 896 (Thermedics). The catheter used in connection with the means of access also has a smooth exterior so that the body tissue in the implantation tunnel forms a tunnel sheathing enclosing the catheter.

German patent 28 06 030 and U.S. Pat. No. 4,588,461 describe vascular prostheses consisting of a porous hose made of a non-woven fiber fabric of fine polyurethane fibers. Body tissue will grow onto such vascular prostheses. Vascular prostheses replace blood vessels or other vessels in the body that had to be removed, for example, because of thrombosis. Accordingly, vascular prostheses are set into the body of a patient completely. The means of access described in European Patent Application 0 164 896 has two non-woven layers of polyurethane fibers with different porosity that are to allow the growing in of epithelium cells and collagen producing fibroblasts at defined locations in subcutaneous implantation. The non-woven layer with the smaller pore width is disposed on the surface of the "neck" of the means of access and should have a fiber spacing of 75–100 $\mu$m. It is oriented towards the skin and is meant to allow the growing in of epithelium cells. In contrast thereto, the disc-shaped part of the means of access, which is arranged in the subcutaneous range, is defined by a fiber spacing between 400 and 800 $\mu$m and is intended to allow the ingression of fibroblasts which will afterwards from collagen fibers.

It is an object of the present invention to provide a transcutaneous implantation catheter wherein the risk of defensive reactions and infections in the implantation tunnel is reduced. It is a further object of the present invention to provide a transcutaneous implantation catheter in which the cells intended to grow into the catheter shall dispose of the necessary space between the fibers even if the catheter has not been implanted by a surgeon with perfect accuracy, but has been positioned only approximately at the precise location, for example, by means of the stylet technique.

SUMMARY OF THE INVENTION

In the transcutaneous catheter of the present invention, the outer surface of the second (intermediate) section consists of a porous non-woven fiber fabric onto which tissue of the body may directly grow. Thus, the peritoneal tissue will uniformly grow onto the second section over the entire length of the second section. Body tissue will grow onto the second section of the catheter and sealingly enclose the same. Due to the low irritation by foreign bodies and to the absence of giant cells, fibroblasts will enter the wall of the second catheter section for a period of up to several months after the implantation, which will then also start to produce collagen. Bundles of collagen fibers provide a capsule-like connection between the catheter and the surrounding tissue. This capsule is easily detachable. Thus, the catheter is integrated into the receiving tissue over the entire length of the second section. The second section preferably is about 5 cm in length. The inner diameter of the second section preferably is about 4 mm with a wall thickness of about 1 mm.

In the catheter of the present invention, fibroblasts diffuse into the loose non-woven fabric, thereby producing a collagen matrix that adheres to the insertion channel. The collagen fibrils stop the unhemmed wandering of skin epithelium cells that would otherwise grow downwards beside the hose surface, thereby forming a pocket around the catheter which would leave the catheter lying in a sheathing channel without any connection to the skin. Further, the skin epithelium cells can enter between the fabric fibrils until the distance between the fibers becomes too small and the concretion comes to a halt.

As has been shown in tests on animals, a fabric with a uniform fiber spacing of about 80 to 100 $\mu$m from the lowermost to the uppermost layer is disadvantageous in some instances. This is due to the fact that the giant foreign body cells lying on the fiber array cause a complete sealing because of the short distances between the fibers, thereby preventing further fibroblast immigration. Only a gradual loosening of the fabric structure, i.e. the space between the fibers slowly increase from the inside to the outside, causes a better ingrowing reaction. Now, the giant foreign body cells no longer cover all gaps in the fabric, the fibroblasts diffuse into the fabric and a collagen connection is obtained in the deeper layers. On the skin level, skin epithelium cells enter the fabric and form a concretion therewith. However, since skin cells and fibroblasts are of different size (skin epithelium cells about 5–10 $\mu$, fibroblasts 40–50 $\mu$), different distances between the fibers are necessary in the different growing-in levels.

However, if the catheter is to be placed in a body cavity using, as is often done, either the Seldinger, the stylet or the puncture set technique, where a portion of the catheter is drawn through (or "tunneled") under the skin, it may be expected that the orientation of the "correct" fiber spacing in the fabric to the tissue will not always be exactly such that the process of concretion can take place as intended. This can only be ensured if all required fiber spacings (narrow spacings for epithelium cells and larger spacings for fibroblasts) are provided at all locations of the tunneling zone.

Preferably, the third section of the hose consists of the same material as the second section; however, the third section has its surface provided with a continuous smooth coating. The coating prevents contaminations from entering the extracorporal third catheter section and it also imparts a greater stiffness to this section, compared to the second section. The second section is softer and more flexible than in the known catheters so that bending the catheter in the implantation tunnel is facilitated and the restoring forces acting on the implantation tunnel walls are reduced. The tissue is not irritated by the soft second section. The first section lying in a body cavity, such as a blood vessel, the peritoneum or the bladder, has a smooth closed surface. Since this section lies in the body cavity and is not meant for body tissue to grow in, it may be somewhat stiffer than the second section.

The transcutaneous implantation catheter of the present invention is suited for use as a permanent catheter, in particular in continuous ambulant peritoneal dialysis (CAPD).

BRIEF DESCRIPTION OF THE DRAWINGS

The following is a detailed description of one embodiment of the present invention in the form of a peritoneal catheter, the description being taken in conjunction with the accompanying drawings. Instead of the peritoneum, other body cavities may be catheterized.

DESCRIPTION OF THE PREFERRED EMBODIMENTS

Figure 1:
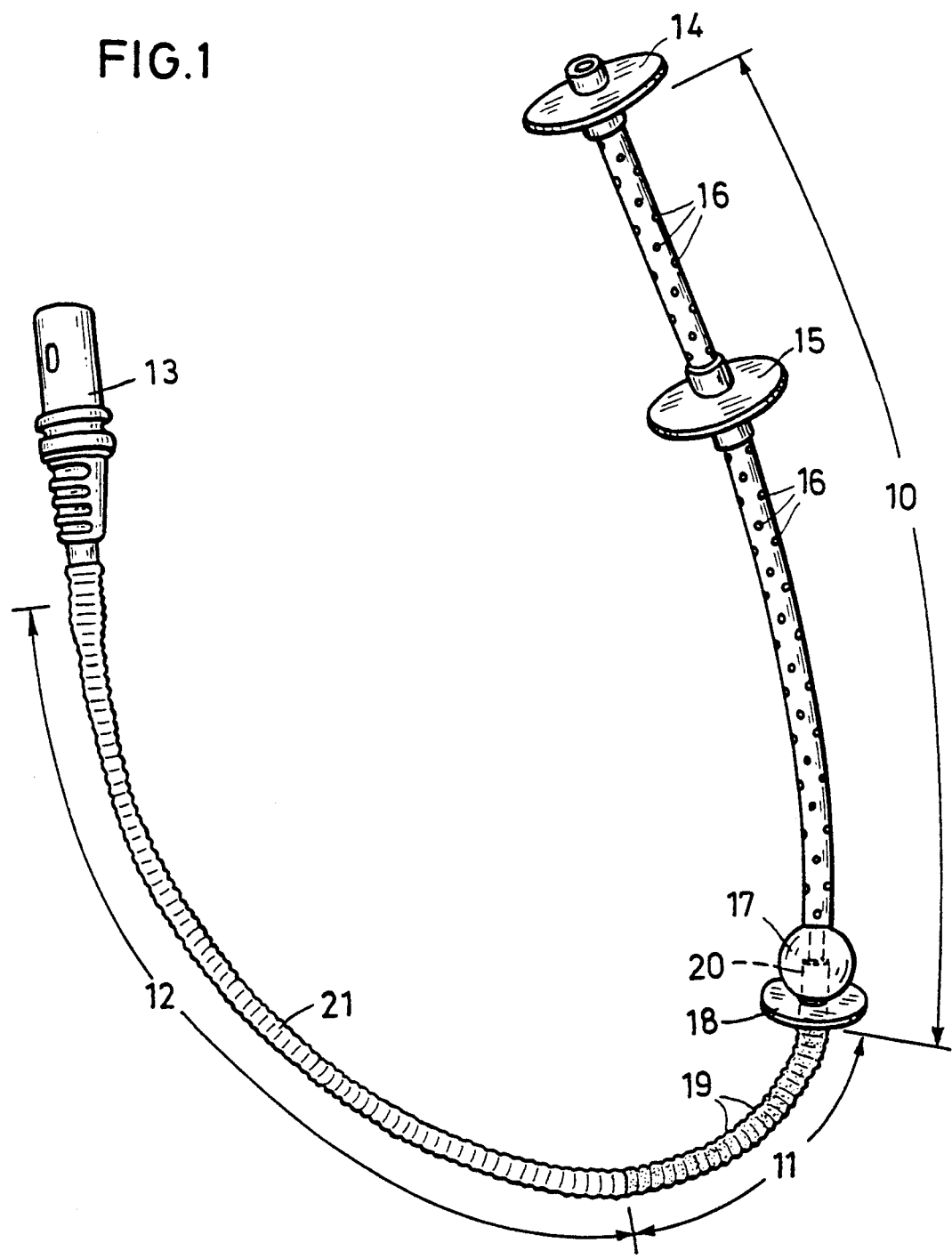
FIG. 1 is a view of a peritoneal catheter.

The catheter illustrated in FIG. 1 consists of a hose having an inner diameter that is substantially constant over the entire length. The hose has an intraperitoneal first section 10, a second section 11 for allowing the skin and muscle tissue to grow in and an extracorporal third section 12. A connector 13 is fixed at the end of the third section 12.

In a manner known per se, the first section 10 is provided with two projecting discs 14, 15 which are spaced from each other in the longitudinal direction of the hose. It is the purpose of these retaining discs to retain the catheter in the area of the Douglas pouch. The first section 10 has numerous holes 16 provided therein for the inflow and the outflow of liquid. Further, one end of the section 10 is open. The end opposite the open end of the section 10 is provided with a sealing ball 17 that will rest below the rear fascia of the musculus rectus. The sealing ball 17 is joined immediately by the second section 11 that has a radially projecting disc 18 abutting the sealing ball 17 and provided for being grown around by the peritoneum and for sealing the same.

Alternatively, an annular groove 50 may be provided in a portion of the catheter adjacent the first and second sections for enabling suturing and the growth of tissue onto a passage into the body cavity.

However, other retaining devices, as known from other catheters, may be used instead of the retaining discs. These may include, without limitation, pigtail coils, Malecot or Pezzer shields or balloons.

Instead of the sealing ball and disc, one may also use an abutment or a set-on ring with a circumferential groove.

The second section 11 consists of a sleeve of a nonwoven fiber fabric made of thin polyurethane fibers. This fiber fabric may be produced according to the method of German Laid Open Patent Application 28 06 030 by winding a plurality of threads. These thin threads with a thickness of approximately 4 to 5 $\mu$m are produced by spraying technology. In this technology, a polyurethane solution is blown from a nozzle and the resulting threads are wound upon a rod or a shaft. In doing so, an irregular net structure of threads is obtained, the threads adhering to each other at the crossing points. Due to the spraying conditions selected, the fiber spacing increases from the bottom to the top. It may increase continuously or stepwise. For example, the lowermost layer is preferably manufactured with a fiber spacing of 40 to 60 $\mu$, the intermediate layer with a fiber spacing of 80 to 100 $\mu$ and the uppermost layer with a fiber spacing of 200 to 600 $\mu$. Other combinations and steps are possible. The thickness of the respective layers is about 0.7 to 0.5 mm. For the definition of the fabric porosity, it has been found that the flow time of a medium under defined pressure conditions through a unit surface provides a better measure than the definition of mean fiber spacings. In order to prevent kinking, a helical reinforcing thread 19 is provided in the sleeve thus obtained, making use of the method described in German Laid Open Patent Application 33 45 513 A1 so that the individual windings of the threads will have the required distance to each other. The section 11 of the hose is configured fibrillarily and with open pores, i.e. the structure of the fabric extends over the entire thickness of the hose wall.

The section 11 preferably has a length of about 5 cm and preferably has approximately the same outer diameter as the first section 10 or the third section 12. The section 11 preferably integrally merges with the extracorporal third section 12, which consists of the same material as the section 11, but which is provided with a tight and smooth coating 21 on the outside. The coating 21 imparts a rigidity to the section 12 that is slightly greater than that of the very soft and flexible second section 11.

Figure 2:
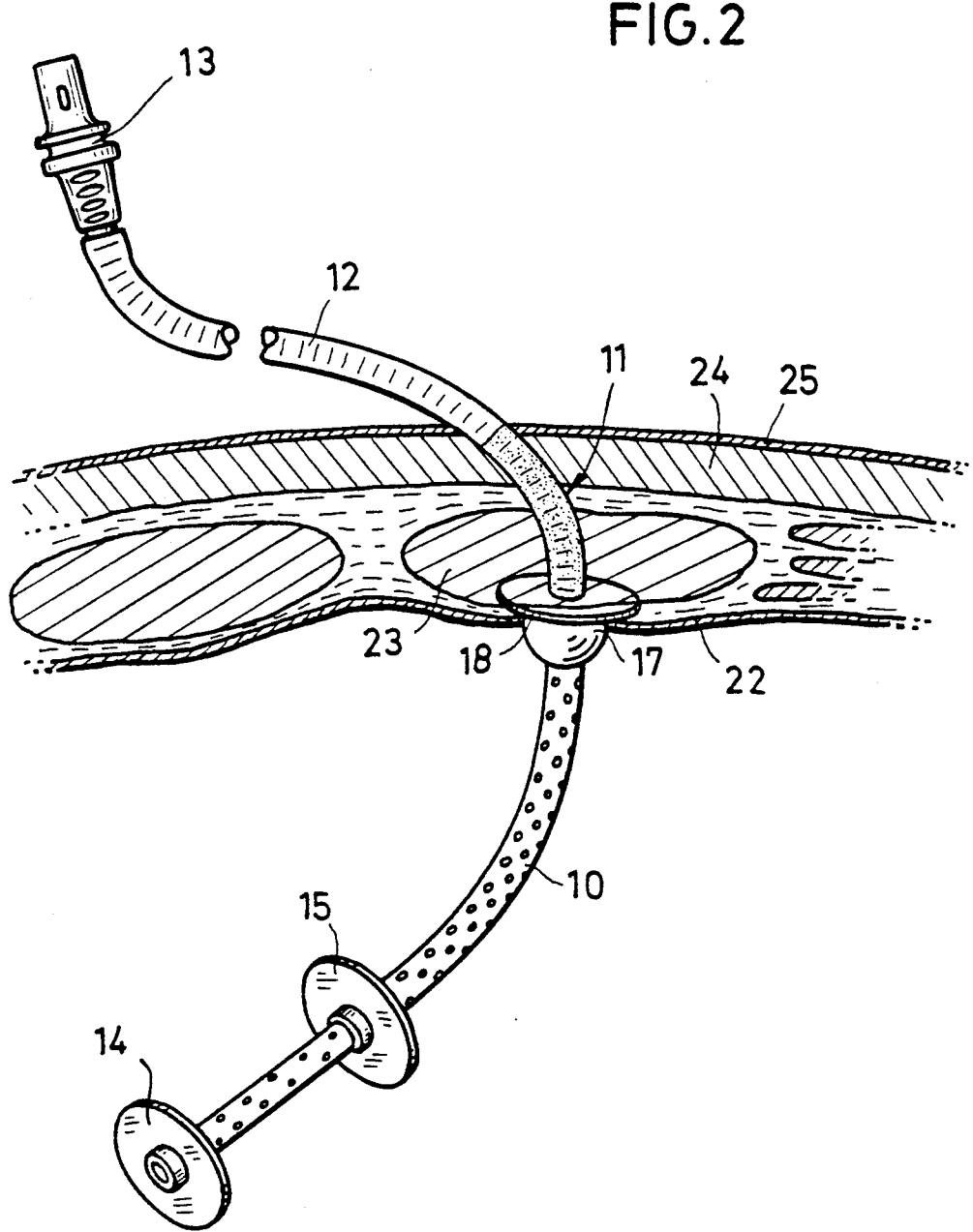
FIG. 2 is an illustration of the position of the catheter after implantation.

FIG. 2 illustrates the catheter when implanted, it being evident that the sealing ball 17 is arranged as an abutment below the peritoneum 22. After the ball 17 has been inserted, the opening in the peritoneum is sutured, with the catheter going therethrough. The section 11 leads through the musculus rectus 23, the disc 18 which consists of the fiber material of the second section 11 being supported on the peritoneum 22 and being ready to be grown around by tissue. The second section 11 further extends through the subcutis and the cutis 25. The third section 12 of the catheter lies outside the body.

Figure 3:
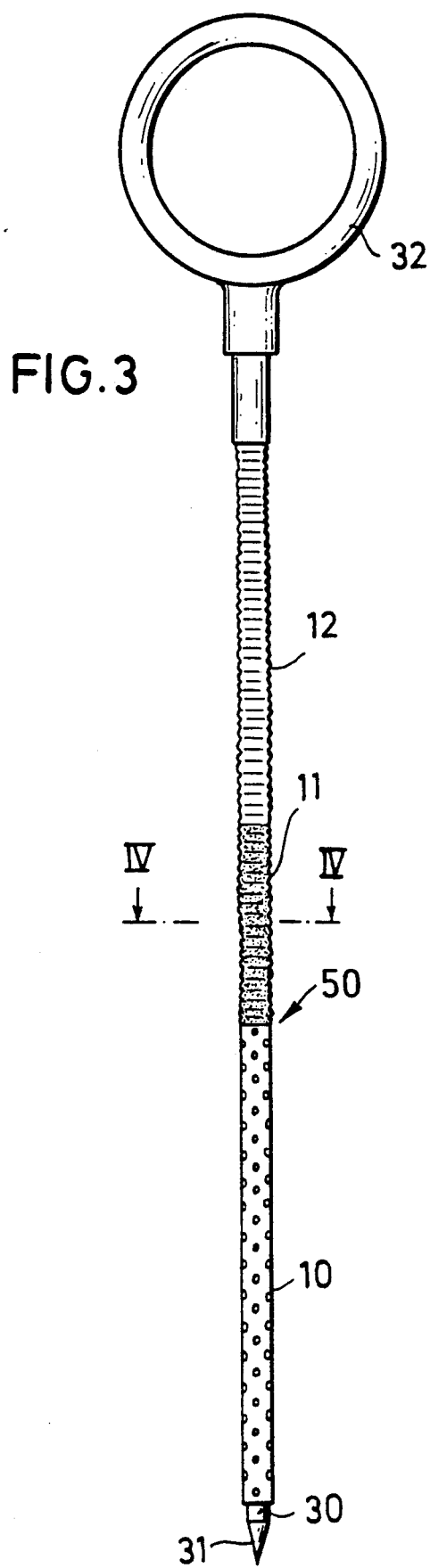
FIG. 3 is a view of a stylet catheter.

FIG. 3 illustrates a catheter with the same sections as shown in FIGS. 1 and 2, but there are no discs and balls set on the catheter. The catheter is arranged on a stylet 30, the sharp tip 31 of which protrudes from the catheter and which has handle 32 at its rear end. The CAPD catheter is set by puncturing.

Figure 4:
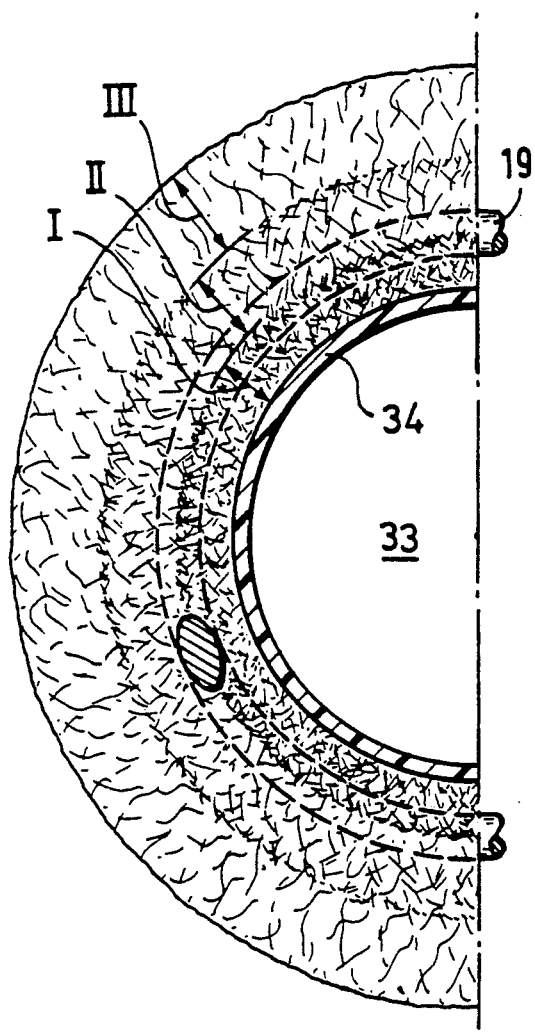
FIG. 4 is a cross sectional view of the fleece zone along line IV—IV in FIG. 3.

FIG. 4 is a cross section of a catheter as shown in FIGS. 1 to 3 taken through the fabric zone 11, as for example the section IV—IV in FIG. 3. The Figure illustrates the inner lumen 33 of the catheter that has a fluidtight inner coat 34, the coat being joined by the successive fleece zones I, II and III characterized by increasing fiber spacing.

The lowermost fleece zone I features a fiber spacing of about 40 to 60 μ and is about 0.2 mm thick; thereabove lies the zone II with a fiber spacing from about 80 to 100 μ and a thickness of about 0.4 mm; the uppermost layer, zone III, has a fiber spacing of 200 to 600 μ and a thickness of 0.4 mm. The fiber spacings indicated are the respective "mean fiber spacings".

Preferably, the second section 11 contains a helically extending reinforcing strand or wire 19. This helical reinforcement serves to improve the resistance to kinking in narrow bends. Despite an increased resistance to kinking, there is a lesser radical restoring force of the catheter in the tunneling zone, thereby preventing a necrotization of the surrounding tissue. The helical reinforcement is embedded into the fiber fabric. The fluidtight wall 34 (FIG. 4) forms but a thin coating at the inside of the tubular fiber fabric, yet not a hose in itself. Thus, it does not have a substantial reinforcing function. The reinforcement is mostly performed by the helical reinforcing strand 19 that is designed such that the compressibility in the section 11 is lower than in the other sections of the catheter. The restoring capacity in section 11 is also lower than in the other sections of the catheter.

We claim:

1. A transcutaneous implantation catheter for implantation in a tunneling zone in a body cavity, comprising:
    a first section configured for intracorporal placement,
    a second substantially tubular section configured for implantation in the tunneling zone, and
    a third section configured for extracorporal placement,
    the second section defining an inside and an outside and comprising a non-woven fiber fabric having a fibrillary open-pore structure defining a mean fiber spacing,
    the mean fiber spacing increasing from the inside of the second section to the outside of the second section.

2. A transcutaneous implantation catheter for implantation in a tunneling zone in a body cavity, comprising:
    a first section configured for intracorporal placement,
    a second section configured for implantation in the tunneling zone, and
    a third section configured for extracorporal placement,
    the second section defining an inside and an outside and comprising a non-woven fiber fabric having a fibrillary open-pore structure defining a mean fiber spacing,
    the mean fiber spacing increasing from the inside of the second section to the outside of the second section,
    wherein the mean fiber spacing increases in steps from the inside of the second section to the outside of the second section.

3. The transcutaneous implantation catheter of claim 1, wherein the second and third sections are integrally formed and are made of the same material and wherein the third section comprises a closed smooth sheathing.

4. The transcutaneous implantation catheter of claim 1, comprising auxiliary means provided between the first and second sections for enabling suturing and the growth of tissue onto a passage into the body cavity.

5. The transcutaneous implantation catheter of claim 4, wherein the auxiliary means comprises a disc.

6. The transcutaneous implantation catheter of claim 4, wherein the auxiliary means comprises a ball.

7. The transcutaneous implantation catheter of claim 4, wherein the auxiliary means comprises a portion of the catheter defining an annular groove therein.

8. The transcutaneous implantation catheter of claim 1, wherein the second section comprises a helically extending reinforcing thread.

9. A transcutaneous implantation catheter for implantation in a tunneling zone in a body cavity, comprising:
    a first section configured for intracorporal placement,
    a second section configured for implantation in the tunneling zone, and
    a third section configured for extracorporal placement,
    the second section defining an inside and an outside and comprising a non-woven fiber fabric having a fibrillary open-pore structure defining a mean fiber spacing,
    the mean fiber spacing increasing from the inside of the second section to the outside of the second section,
    wherein the fiber fabric comprises fibers having a thickness of between approximately 4 μm and 5 μm.

10. The transcutaneous implantation catheter of claim 1, wherein the fiber fabric comprises polyurethane.

11. A transcutaneous implantation catheter for implantation in a tunneling zone in a body cavity, comprising:
    a first section configured for intracorporal placement,
    a second section configured for implantation in the tunneling zone, and
    a third section configured for extracorporal placement,
    the second section defining an inside and an outside and comprising a non-woven fiber fabric having a fibrillary open-pore structure defining a mean fiber spacing,
    the mean fiber spacing increasing from the inside of the second section to the outside of the second section, wherein the second section is softer and more flexible than the first section.

12. The transcutaneous implantation catheter of claim 1, wherein the second section defines a length of about 5 cm.

13. A transcutaneous implantation catheter for implantation in a tunneling zone in a body cavity, comprising:
    a first section configured for intracorporal placement,
    a second section configured for implantation in the tunneling zone, and
    a third section configured for extracorporal placement, the second section defining an inside and an outside and comprising a non-woven fiber fabric having a fibrillary open-pore structure defining a mean fiber spacing.

the mean fiber spacing increasing from the inside of the second portion to the outside of the second section, wherein the mean fiber spacing in the fiber fabric increases from the inside of the second section to the outside of the second section in a range from about 40 μm to about 600 μm.

14. The transcutaneous implantation catheter of claim 1, wherein the first section comprises flexible solid plastic material.

* * * * *